US010286136B2

(12) United States Patent
Gronau et al.

(10) Patent No.: US 10,286,136 B2
(45) Date of Patent: May 14, 2019

(54) METHOD AS WELL AS APPARATUSES FOR TESTING AT LEAST ONE FUNCTION OF A MEDICAL FUNCTIONAL DEVICE (71) Applicant: Fresenius Medical Care Deutschland GmbH, Bad Homburg (DE)

(72) Inventors: Soeren Gronau, Rüsselsheim (DE); Joachim Manke, Loehnberg (DE); Ralf Mueller, Bad Homburg (DE); Ingo Schaefer, Eschborn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/990,084

(22) Filed: May 25, 2018

(65) Prior Publication Data
US 2018/0272053 A1    Sep. 27, 2018

Related U.S. Application Data (63) Continuation of application No. 15/200,267, filed on Jul. 1, 2016, now Pat. No. 10,004,837, which is a (Continued)

(30) Foreign Application Priority Data

Jul. 29, 2011    (DE) .......................... 10 2011 108 784

(51) Int. Cl.
*A61M 1/16*    (2006.01)
*A61M 1/34*    (2006.01)
(Continued)

(52) U.S. Cl.
CPC ............ *A61M 1/1621* (2014.02); *A61M 1/14* (2013.01); *A61M 1/1605* (2014.02); *A61M 1/34* (2013.01);
(Continued)

(58) Field of Classification Search
CPC .................. A61M 1/34; G01L 27/00
See application file for complete search history.

(56) References Cited

U.S. PATENT DOCUMENTS 5,674,404 A * 10/1997 Kenley .................... A61L 2/04
210/741
6,004,509 A * 12/1999 Dey ........................ A61B 90/40
134/22.12
(Continued)

FOREIGN PATENT DOCUMENTS

CN    2253504    4/1997
CN    101687069    3/2010
(Continued)

OTHER PUBLICATIONS

International Search Report in International Application No. PCT/EP2012/003190, dated Nov. 20, 2012, 7 pages (with English translation).
(Continued)

*Primary Examiner* — Paul M. West
*Assistant Examiner* — Mark A Shabman
(74) *Attorney, Agent, or Firm* — Fish & Richardson P.C.

(57) ABSTRACT

The invention relates to a method for testing at least one function of a medical functional device which is inserted in and connected and compressed with a medical treatment apparatus, and/or a function of this treatment apparatus, wherein between a hydraulic device or a pneumatic unit of the treatment apparatus and the functional device at least one fluid communication is established. It further relates to a detection device which is programmed and/or configured for executing the method according to the invention as well as a medical treatment apparatus which comprises at least one detection device and/or is in signal transmission or is connected for signal transmission with it, a digital storage
(Continued)

medium, a computer program product as well as a computer program.

25 Claims, 2 Drawing Sheets

Related U.S. Application Data continuation of application No. 13/559,873, filed on Jul. 27, 2012, now Pat. No. 9,393,358.

(60) Provisional application No. 61/512,984, filed on Jul. 29, 2011.

(51) Int. Cl.
*A61M 1/14* (2006.01)
*A61M 39/24* (2006.01)
*A61M 1/36* (2006.01)

(52) U.S. Cl.
CPC ........ *A61M 1/3413* (2013.01); *A61M 1/3434* (2014.02); *A61M 1/3607* (2014.02); *A61M 39/24* (2013.01); *A61M 2205/12* (2013.01); *A61M 2205/15* (2013.01); *A61M 2205/18* (2013.01); *A61M 2205/27* (2013.01); *A61M 2205/3306* (2013.01); *A61M 2205/3331* (2013.01); *A61M 2205/3368* (2013.01); *A61M 2205/50* (2013.01); *A61M 2205/70* (2013.01)

(56) References Cited

U.S. PATENT DOCUMENTS

| | | | | |
|---|---|---|---|---|
| 6,066,261 | A * | 5/2000 | Spickermann | A61M 1/16 210/645 |
| 2002/0011449 | A1 | 1/2002 | Muller et al. | |
| 2004/0223857 | A1 | 11/2004 | Kline et al. | |
| 2005/0126998 | A1 * | 6/2005 | Childers | A61M 1/28 210/646 |
| 2005/0131332 | A1 * | 6/2005 | Kelly | A61M 1/1696 604/4.01 |
| 2005/0230292 | A1 * | 10/2005 | Beden | A61M 1/1037 210/85 |
| 2006/0254982 | A1 * | 11/2006 | Kopperschmidt | A61M 1/342 210/646 |
| 2007/0253463 | A1 | 11/2007 | Perry et al. | |
| 2010/0130905 | A1 * | 5/2010 | Nurnberger | A61M 1/3672 604/6.07 |
| 2010/0191164 | A1 * | 7/2010 | Sasaki | A61M 1/16 604/5.04 |
| 2010/0192686 | A1 * | 8/2010 | Kamen | A61M 1/16 73/290 R |
| 2010/0274168 | A1 | 10/2010 | Gronau et al. | |
| 2011/0166507 | A1 | 7/2011 | Childers | |
| 2012/0022441 | A1 * | 1/2012 | Kelly | A61M 1/1696 604/29 |
| 2013/0028788 | A1 * | 1/2013 | Gronau | A61M 1/34 422/44 |
| 2013/0037485 | A1 * | 2/2013 | Wilt | A61M 1/1037 210/646 |
| 2013/0174650 | A1 * | 7/2013 | Wiktor | A61M 1/16 73/40.5 R |

FOREIGN PATENT DOCUMENTS

| | | |
|---|---|---|
| CN | 10171172 | 5/2010 |
| CN | 101801432 | 8/2010 |
| DE | 19757523 | 4/1999 |
| DE | 10034711 | 2/2002 |
| DE | 102007024463 | 11/2008 |
| DE | 102007042964 | 3/2009 |
| DE | 102009012632 | 9/2010 |
| DE | 102009024468 | 12/2010 |
| DE | 102010020838 | 11/2011 |
| DE | 102010032182 | 1/2012 |
| EP | 0165751 | 9/1986 |
| EP | 0407737 | 1/1991 |
| EP | 1309417 | 5/2003 |
| EP | 1595560 | 11/2005 |
| EP | 2174677 | 4/2010 |
| JP | S61-008057 | 1/1986 |
| JP | H11-253550 | 9/1999 |
| JP | 2006-255331 | 9/2006 |
| JP | 2007-029705 | 2/2007 |
| JP | 2012-192101 | 10/2012 |
| WO | WO 02/014001 | 2/2002 |

OTHER PUBLICATIONS

International Preliminary Report on Patentability in International Application No. PCT/EP2012/003190, dated Feb. 4, 2014, 7 pages.

* cited by examiner

METHOD AS WELL AS APPARATUSES FOR TESTING AT LEAST ONE FUNCTION OF A MEDICAL FUNCTIONAL DEVICE

CROSS-REFERENCE TO RELATED APPLICATIONS

This application is a continuation application of and claims priority to U.S. application Ser. No. 15/200,267, filed Jul. 1, 2016, which is a continuation of and claims priority to U.S. application Ser. No. 13/559,873, filed Jul. 27, 2012, issued as U.S. Pat. No. 9,393,358, which claims priority to, and the benefit of, U.S. Provisional Application 61/512,984 filed on Jul. 29, 2011, and German Patent Application DE 10 2011 108 784.6 filed on Jul. 29, 2011. The contents of each application is incorporated herein by reference in its entirety.

FIELD OF THE INVENTION

The present invention relates to methods and apparatuses for testing at least one function of a medical functional device which is inserted in and connected and compressed with a medical treatment apparatus, and/or a function of this treatment apparatus, wherein between a hydraulic device or a pneumatic unit of the treatment apparatus and the functional device at least one fluid communication is established.

BACKGROUND OF THE INVENTION

From practice, machine-based tests for testing the function and reliability of medical functional devices such as extracorporeal blood tubes, blood cassettes and the like are known. Such a test is known as a pressure maintenance test or pressurizing test. It is performed after the functional device in question is or was connected with the treatment apparatus, i.e. after the treatment apparatus has already been set up with the functional device, and before the treatment of the patient starts.

One object of the present invention is to provide another method for testing the function of medical functional devices. Furthermore, suitable apparatuses, a suitable digital storage medium, a suitable computer program product and a suitable computer program are to be specified.

SUMMARY OF THE INVENTION

In one embodiment there is provided a method for testing at least one function of a medical functional device which is inserted in and connected and pressed with a medical treatment apparatus, and/or a function of this treatment apparatus, wherein between a hydraulic device or a pneumatic unit of the treatment apparatus and the functional device at least one fluid communication is established, wherein the method comprises the steps:
  building up a pressure by means of the hydraulic device or a pneumatic unit within the fluid communication;
  measuring a pressure prevailing within the fluid communication or a pressure change; and
  making a statement about the tested function of the functional device based on a comparison of the prevailing pressure or the measured pressure change with previously saved values, threshold values, ranges or developments.

The method may further comprise the step:
building up the pressure by means of a substitute pump of the treatment apparatus.

In an alternative embodiment the method may further comprise the steps:
  determining a pressure drop or a pressure rise within the fluid communication;
  determining a patency of the fluid communication or of the functional device based on a comparison of the determined pressure drop or pressure rise with previously saved values, threshold values, ranges or developments.

In another embodiment the method may further comprise the steps:
  determining a pressure drop or a pressure rise within the fluid communication;
  determining a tightness of the fluid communication or of the functional device based on a comparison of the determined pressure drop or pressure rise with previously saved values, threshold values, ranges or developments.

In yet another embodiment the method may further comprise the step:
  filling an extracorporeal blood circuit which is connected with the functional device before building up the pressure.

In another embodiment the method may further comprise the step:
  blocking treatment modalities and/or restricting treatment parameters of the treatment method taking into account a result of the test of at least one function of the medical functional device and/or the treatment apparatus, wherein the result was achieved by means of the present method.

The above methods may be executed before the beginning of a treatment of a patient during which the functional device is used.

In another embodiment there is provided a detection device, programmed and/or configured for executing or prompting the method for testing at least one function of a medical functional.

In yet another embodiment there is provided a medical treatment apparatus which comprises at least one detection device for testing at least one function of a medical functional and/or is in signal transmission or is connected for signal transmission with it.

In another embodiment there is provided a digital storage medium, in the form of a disk, CD or DVD or EPROM, with electronically readable control signals, configured for interacting with a programmable computer system such that the mechanical steps of the method for testing at least one function of a medical functional are prompted.

In another embodiment there is provided a computer program product with a program code saved on a machine-readable medium for prompting the mechanical steps of the method for testing at least one function of a medical functional when the computer program product runs on a computer.

In another embodiment there is provided a computer program with a program code for prompting the mechanical steps of a method for testing at least one function of a medical functional when the computer program runs on a computer.

DETAILED DESCRIPTION

A method is provided for testing at least one function of a medical functional device which is inserted in and connected with—in particular in fluid communication—a medical treatment apparatus, and/or for testing a function of the treatment apparatus which is connected with the functional device.

The method may encompass inserting the functional device into the medical treatment apparatus.

Further, the method may encompass pressing, biasing, pretensioning or prestressing or preloading, or clamping the functional device in the treatment apparatus, for example by means of the door of the treatment apparatus. Alternatively, this is required.

Furthermore, the method may encompass establishing at least one fluid communication between a hydraulic device or a pneumatic unit of the treatment apparatus and the functional device. Alternatively, this condition has already been achieved before the procedure starts.

The method according to the present invention encompasses building up a pressure by means of the hydraulic device or a pneumatic unit within the fluid communication. It additionally encompasses subsequently measuring a pressure which prevails within the fluid communication or of a pressure change such as a pressure rise or a pressure drop after the pressure has been build-up.

Further, the method according to the present invention encompasses making a statement about (assessing) the tested function of the functional device based on a comparison of the prevailing pressure or the measured pressure change with previously saved values, threshold values, ranges or developments.

The detection device according to the present invention is suitable and provided and/or designed and/or configured for executing the method according to the present invention.

The medical or medical-technical treatment apparatus according to the present invention (hereafter also shortened to: treatment apparatus) comprises at least one detection device and/or is connected herewith in signal transmission or is in signal transmission relation with it.

A digital, particularly a non-volatile storage medium according to the present invention, particularly in the form of a machine-readable data storage device, particularly in the form of a disk, CD or DVD or EPROM, with electronically readable control signals may interact with a programmable computer system such that the mechanical steps of the method according to the present invention are prompted or executed.

In doing so, all, a few or some of the mechanically executed steps of the method according to the present invention may be prompted or executed.

A computer program product according to the present invention comprises a program code, volatile, transitorily or non-transitorily stored on a machine-readable storage device for prompting the mechanical steps of the method according to the present invention when the computer program product is executed or runs on a computer. According to the present invention a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

The term machine-readable storage device, as used herein, denotes in certain embodiments of the present invention a storage device which contains data or information which is interpretable by software and/or hardware. The storage device may be a data storage device such as a disk, a CD, DVD, a USB stick, a flashcard, an SD card and the like.

A computer program according to the present invention comprises a program code for prompting the mechanical steps of the method according to the present invention when the computer program runs on a computer. A computer program according to the present invention can be understood as, for example, a physical software product, which is ready for distribution and contains a computer program.

It also applies for the computer program product according to the present invention and the computer program according to the present invention that all, a few or some of the mechanically executed steps of the method according to the present invention are prompted.

In all of the following embodiments, the use of the expression may be or may have and so on, is to be understood synonymously with preferably is or preferably has, respectively, and so on, and is intended to illustrate an embodiment according to the present invention.

Advantageous developments of the present invention are each subject of dependent claims and embodiments.

Embodiments according to the present invention may comprise one or more of the features named hereafter.

In some embodiments according to the present invention, there is wait period for a predetermined standby time or idle time, or measurement time before a statement is made about the tested function.

Measuring a pressure or a pressure change may encompass any kind of determining, for example measuring by means of a sensor, calculating, concluding based on numerical values of other parameters or conditions, and so on.

Similarly, determining, as used herein, can include examining an existance or non-existance, measuring, concluding or achieving, detecting, determining and the like.

In some embodiments according to the present invention the apparatuses, devices and other components comprise the apparatuses, devices and other components necessary for executing the steps of the method or of the test as described herein, or are connected therewith.

In certain embodiments of the method according to the present invention, building up a pressure by means of the hydraulic device or the pneumatic unit within the fluid communication is only carried out when or if a pre-pressure which was previously applied and which is lower than the pressure to be built up no function deviation—or a too large function deviation as compared to a default—was determined or observed. A too large function deviation is present or observed when, for example, a leakage is detected already upon applying a pre-pressure.

In some embodiments according to the present invention the method encompasses filling, in particular complete filling, of the dialysate side and/or the blood side of a blood filter which the functional device is connected with in fluid communication.

In certain embodiments according to the present invention, the method encompasses building up the pressure by means of a substitute pump of the treatment apparatus.

In some embodiments according to the present invention the method encompasses building up the pressure against the substitute pump which stands still or is at best conveying in a defined manner or at a pre-defined rate.

In some embodiments according to the present invention, the method encompasses determining or measuring a pressure drop or a pressure rise within the fluid communication. It further encompasses that a patency (or lacking patency) of the fluid communication or the functional device is determined or postulated based on a comparison of the determined pressure drop or pressure rise with previously saved or stored values, threshold values, ranges or developments.

In certain embodiments according to the present invention the method encompasses determining or measuring a pressure drop or pressure rise—in particular within a predetermined period of time—within the fluid communication. It further encompasses determining (herein, determining is used or to be understood also synonymously with detecting, postulating, formulating and so on) a tightness or lacking a tightness of the fluid communication or the functional device. This determining is based on a comparison of the determined pressure drop or pressure rise with previously saved values, threshold values, ranges or developments.

In certain embodiments according to the present invention, determining a pressure drop or pressure rise within the fluid communication takes place within a predetermined period of time.

In some embodiments according to the present invention the method encompasses conveying a predetermined feed volume within the fluid communication with an automatic substitute connector being connected, the volume being conveyed while the substitute pump runs in reverse direction against a non-return valve which is provided within a substitute channel or by means of the substitute pump conveying in reverse direction against a non-return valve which is provided within a substitute channel. The method of these embodiments further encompasses determining a pressure change within the fluid communication. It additionally encompasses determining a non-return function (or malfunction) of the non-return valve if or in the event that a determined pressure drop is not equal to or higher than a maximum pressure drop. Alternatively, a pressure rise behind or downstream of the non-return valve can of course be monitored for testing the non-return function.

A pump which is running or conveying in reverse (direction), e.g., a substitute pump, is to be understood as a pump which conveys in a direction which is opposite to the direction (forwards) in which said pump conveys, at least at most of the time, during the treatment of the patient.

In some embodiments according to the present invention, the method encompasses conveying a predetermined feed volume with an automatic, connected substitute connector within the fluid communication with the substitute pump running in reverse against a non-return valve which is provided within a substitute channel. In addition, it encompasses determining a pressure change within the fluid communication as well as determining that the substitute pump conveys or has conveyed forwards, if a determined pressure drop is higher than a maximum pressure drop.

In certain embodiments the method according to the present invention encompasses determining a current or present pressure value of a later, second point of time based on an already available pressure value of a previous, first point of time from a measured value and from a predetermined smoothing factor or multiplier—in particular during a pressure maintenance phase or pressure holding phase—according to the formula:

$$VALUE\_new = VALUE\_old * SF + MEASURED\ VALUE * (1-SF)$$

wherein it applies that:

| | |
|---|---|
| VALUE_new | is a current pressure value; it may be a fictional or calculated value; |
| VALUE_old | is the pressure value which is already available or was determined at an earlier point of time; it may also be a fictional or a value which was calculated—in particular with the formula as discussed here; |
| SF | is a smoothing factor; and |
| MEASURED VALUE | is a currently measured pressure, i.e., a pressure which was measured at a later, second point of time. |

In certain embodiments of the method according to the present invention, the smoothing factor is in a range of 0.9 to 0.96, preferably, it is 0.93.

In some embodiments according to the present invention the method encompasses filling an extracorporeal blood circuit which is connected with the functional device—preferably such that it is free from air—before building up the pressure.

In some embodiments of the method according to the present invention, at least one function, in particular opening, closing or a sealing function, of at least the valve for an addition point for administering substitute in predilution; of a valve for an addition point for administering substituate in postdilution; of a single-needle valve; of a non-return valve in the substituate channel; and/or of an automatic substituate connector is tested.

In certain embodiments according to the present invention, the method is executed before a treatment of a patient in which the functional device is used is started.

In certain embodiments according to the present invention the method encompasses blocking treatment modalities and/or restricting treatment parameters of the treatment method or of the treatment modality. Blocking or restricting takes place based on (or while taking into account) a result of the testing of at least one function of the medical functional device and/or the treatment apparatus by means of the present method.

In some embodiments of the method according to the present invention, the medical functional device is a blood cassette and the treatment apparatus is a blood treatment apparatus.

In some embodiments according to the present invention, the detection device comprises at least one displaying device for displaying a result gained by the method according to the present invention. The displaying device may be a display, an error display, or the like.

In certain embodiments according to the present invention the detection device comprises at least one alarm device for outputting an alarm. The alarm device may be provided or configured for outputting an alarm if or in the event that the result of the execution of the method according to the present invention is not within a predetermined range or values range. The alarm may be an acoustic and/or optical alarm.

In certain embodiments according to the present invention, the detection device is programmed and/or configured to act on the treatment apparatus such that at least one treatment option or treatment modality (for example a dialysis method, in particular as named herein) for which the tested functional device may (also) be used according to its determination or due to its constructional design, and/or treating under predetermined treatment parameters by means of the concrete, tested functional device is not allowed. This holds true in the event that a missing or an insufficient functionality—for example insufficient closing, opening or sealing—of the functional device and/or the treatment apparatus (or a component of each, respectively, in particular of the valve of the addition point for substitute in predilution and/or of a valve of the addition point for substitute in postdilution) was recognized by the course of this method.

In some embodiments according to the present invention the detection device acts on the treatment apparatus such that the treatment option(s) hemofiltration and/or hemodiafiltration are not executable by means of the concrete, tested functional device.

In some embodiments according to the present invention, the detection device is a control or regulating apparatus and/or a function test monitor or comprises such apparatus or monitor or both.

In certain embodiments according to the present invention, the medical treatment apparatus is embodied as a blood treatment apparatus, preferably as an apparatus for apheresis or dialysis, more preferably for hemodialysis, hemofiltration, or hemodiafiltration.

Some or all embodiments according to the present invention may provide for one, some or all of the advantages named above and/or hereafter.

For example, since functions of the utilized articles or items as well as of the treatment apparatus which are security-related are tested according to the present invention, enhanced safety for the patient may be achieved.

Since the method according to the present invention may take place during preparation or set-up of the treatment apparatus, a technical error can be detected already before the patient is connected and before blood has come into contact with the treatment apparatus and the extracorporeal blood circuit. The latter prevents avoidable consumption of disposables. It further allows for an early and, therefore, easy replacement of defect components if an error occurs.

In some embodiments according to the present invention, since the method according to the present invention may take place automatically and without assistance of the personnel in charge, it is advantageously possible to detect errors in a working time-saving manner and already before the beginning of the treatment. In addition, the approach as described herein ensures that relevant test steps or test procedures cannot be forgotten, as this approach is executable in an automated manner.

Hereafter, the present invention is exemplarily described with reference to the appended figures in which identical reference numerals refer to same or similar components.

Figure 1:
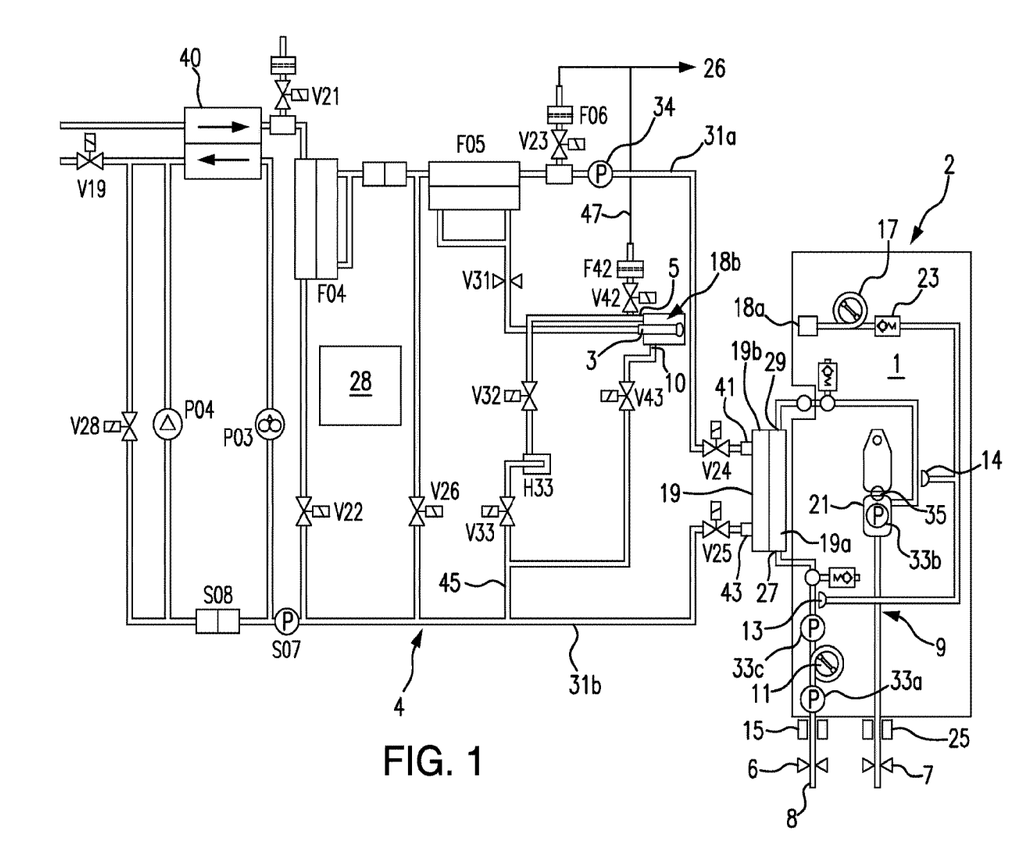
FIG. 1 shows a schematically simplified diagram of a treatment apparatus according to the present invention with a blood cassette which may be tested by means of the present invention.

FIG. 1 shows a diagram of a treatment apparatus according to the present invention with a blood cassette and its components which are explained for a better understanding of the exemplary embodiments which are discussed thereafter.

An extracorporeal blood circuit 1 runs or extends on the exterior or outside and in the interior or inside of a blood cassette 2 and connects it with a treatment apparatus 4. The extracorporeal blood circuit 1 comprises an access device (not shown), for example an arterial connection needle, or it is connected herewith. A fluid flow through the extracorporeal blood circuit 1 or sections hereof may be prevented or inhibited by means of an arterial patient tube clamp 6, which is arranged in its arterial patient tube 8 (also denoted as arterial blood line), furthermore by means of a venous patient tube clamp 7 in its venous patient tube 9 (also denoted as venous blood line).

A section of the extracorporeal blood circuit 1 is inserted into a blood pump 11. The extracorporeal blood circuit 1 comprises an addition point 13 for substitute liquid (in predilution) and an addition point 14 for substitute liquid (in postdilution). Here, the addition points 13 and 14 are exemplarily embodied as phantom valves. Phantom valves of this kind are described in WO 2010/121819, which is incorporated herein by reference in its entirety.

An arterial air-blood detector 15 is provided at the arterial blood line 8.

FIG. 1 further shows a substitute pump 17. It is located downstream of a connection point at which the blood cassette 2 may be connected with its substitute port 18a with an automatic substitute connector 18b of the treatment apparatus 4. The automatic substitute connector 18b comprises in the example of FIG. 1 a first fluid conduct 3, a second fluid conduct 5 and a third fluid conduct 10 for rinsing the automatic substitute connector 18b and for conducting substitute through the automatic substitute connector 18b.

A blood filter 19 with a blood chamber 19a and a dialysate chamber 19b is integrated into the extracorporeal blood circuit 1.

The blood cassette 2 comprises a venous air separation chamber 21.

A substitute line of the blood cassette 2 comprises a non-return valve 23.

The extracorporeal blood circuit 1 comprises a venous air-substitute liquid-blood detector 25 at the venous blood line 9.

The treatment apparatus 4 comprises or is connected with a source of compressed air 26. It further comprises or is connected with a control or regulating device 28

Further, in FIG. 1, a dialyzing liquid supply line 31a which carries dialyzing liquid to the dialysate chamber 19b, and a dialysate drain line 31b which carries dialysate away from the dialysate chamber 19b may be seen.

A pressure sensor 33a is provided upstream of the blood pump 11 in the arterial blood line 8.

A pressure sensor 33b is provided in the area of the venous air separation chamber 21 in the venous blood line 9.

A pressure sensor 33c, also denoted as prefilter pressure sensor, is provided downstream of the blood pump 11 in the arterial blood line 8. It may be arranged upstream of the addition point 13.

The blood cassette 2 comprises a single-needle valve 35.

An again further pressure sensor 37 is located in or at the dialyzing liquid supply line 31a between the source of compressed air 26 and the blood filter 19.

Valves V19, V24, V25, V28, V31, V32 and V33 are provided in sections of the hydraulics of the treatment apparatus 4.

The valve V24 is located in or at the dialyzing liquid supply line 31a.

The valve V25 is located in or at the dialysate drain line 31b.

The valve V28 is located in a drain line 45.

The valve V31 is located in the first fluid conduct 3 of the automatic substitute connector 18b or in a line which leads towards it.

The valve V32 is located in the second fluid conduct 5 of the automatic substitute connector 18b or in a line which leads towards it.

The valve V33 is located in the drain line 45.

The valve V19 is located downstream of all of the previously mentioned valves V24, V25, V28, V31, V32 and V33.

A hydraulic balance chamber 40 is only shown in outlines.

Figure 2:
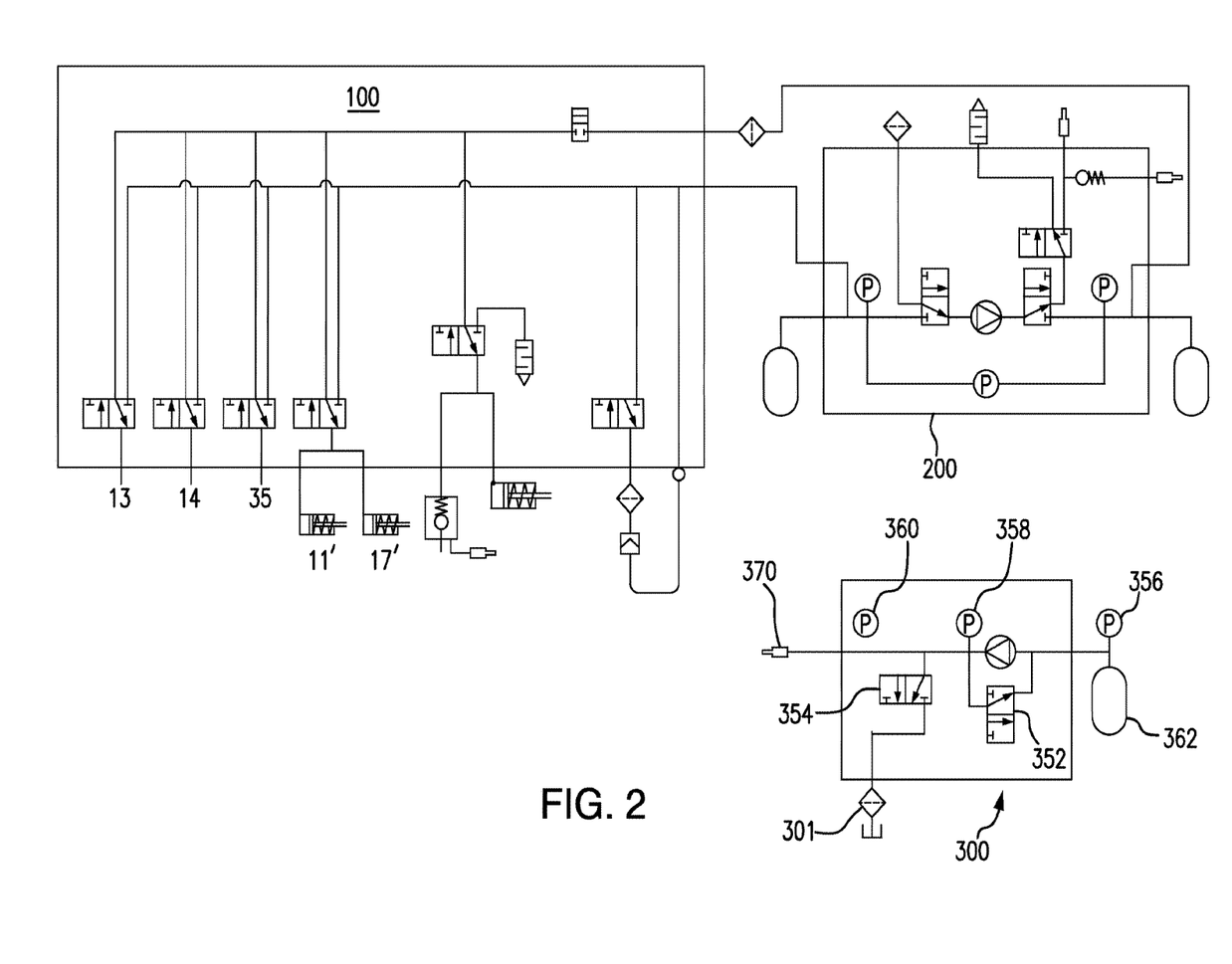
FIG. 2 shows a schematically simplified pneumatics circuit diagram of a treatment apparatus according to the present invention.

FIG. 2 shows a pneumatics circuit diagram of a treatment apparatus according to the present invention. The components shown herein serve again a better understanding of the exemplary embodiments of the present invention which are explained hereafter.

In FIG. 2, an air diffusor panel 100 is illustrated which is connected with a pneumatic unit 200. Further illustrated is a single-needle unit 300.

The air diffusor panel 100 comprises connections to the addition point 13, to the addition point 14, to the single-needle valve 35, to a brake device 11' of the blood pump 11, to a brake device 17' of the substituate pump 17, as well as to further components which are not further discussed here.

The pneumatic unit 200 is connected as a source of compressed air 26 with the hydraulics of the treatment apparatus 4 (see FIG. 1).

The single-needle unit 300 comprises ventilation inlets and outlets 301, a single-needle compressor 350, a bypass valve 352, a vent valve 354, a pressure sensor 356 at the single-needle pressure vessel, a pressure sensor 358 of the SN line, an absolute pressure sensor 360 as well as a temperature sensor 362 in the SN pressure vessel. A connector 370 connects the single-needle unit 300 with the single-needle chamber of the blood cassette 2.

As regards the meanings of the remaining elements which are specified in the figures, it is referred to the reference numeral declaration in list form below.

The following first embodiment relates to a leak test of a disposable, here a blood cassette 2, which does not comprise a single-needle (SN) chamber or in which a single-needle chamber is separated from the extracorporeal blood circuit 1 by means of a single-needle valve 35 and stays separated. Hereby, it is tested whether the blood cassette 2 is tight or sufficiently tight to the exterior. Furthermore, it is tested with the door being closed and pressed and the blood cassette 2 being inserted whether a pressure in the extracorporeal blood circuit 1 (in short also: EB 1, wherein 1 indicates the reference numeral) can be built up and maintained. By means of this test, it may in particular be tested whether the tightness of the extracorporeal blood circuit 1 (without patient tubes) is granted or accomplished, the standstill leakage of both blood pump rollers may be tested, and/or whether sufficient pressing for sealing of the flow paths and its branches is achieved or provided for in the blood cassette 2 may be tested.

In addition, the function of the non-return valve 23 in the substituate channel can also be tested by means of the approach as described below, in particular the functions close and seal of the non-return valve 23 in the blood cassette 2.

For performing the test, the blood cassette 2 is inserted into the treatment apparatus and is pressed against a door of the treatment apparatus by closing this door. The dialyzer or blood filter 19 is connected and filled on the disposable side and on the hydraulic side. The extracorporeal blood circuit 1 is filled with liquid and largely free from air. The EB 1 is alarm-free, the blood system is active, the hydraulics is in a state of preparation, and the dialysate flow is turned on. The arterial patient tube 8 and the venous patient tube 9 are both connected with the rinse port, which is not illustrated here, via a T-piece or T-section.

At the beginning of the test of this embodiment according to the present invention, the automatic substituate connector 18b is in the connection position. The substituate supply lines or the substituate branch is or are filled.

The valve V33 is closed. The hydraulics is put into the so-called Extended Bypass (valves V24, V25 are out of service or dead or not energized). Valve V31 is open. The arterial patient tube clamp 6 and the venous patient tube clamp 7 are open (energized). The predilution valve 13 and the postdilution valve 14 are open; the single-needle valve 35 is closed.

If the pressure in the hydraulics exceeds the predetermined pressure PTESTSTART_HYD (measured by means of the pressure sensor 37, arranged at the dialyzing liquid supply line 31a), it is relieved or released with the aid of the substituate pump 17. For this, V33 is opened and substituate is conveyed until the hydraulic pressure (measured also by means of the pressure sensor 37) has fallen below the pressure PTESTSTART_HYD. Subsequently, the substituate pump 17 is stopped and V33 is closed again.

If the pressure in the hydraulics does not exceed the predetermined pressure PTESTSTART_HYD, it is tested whether the pressure in EB 1 exceeds the predetermined pressure PTESTSTART_EB (measured at the pressure sensor 33b in the area of the venous air separation chamber 21). If this is the case, it is relieved or released by opening the valve V33 of the hydraulics; subsequently, the valve V33 is closed.

After that, the blood pump rotor of the blood pump 11 is positioned such that only a first roller of the pump rotor is engaged with the extracorporeal blood circuit 1. Then, both the arterial patient tube clamp 6 and the venous patient tube clamp 7 are closed and a predetermined idle time PRESSURE BALANCE TIME is waited for pressure balance, and the arterial initial pressure (measured by means of the pressure sensor 33a of the arterial blood line) is noted for determining the leakage during roller standstill.

Liquid is conveyed into the EB 1 with the substituate pump 17 at a predetermined flow SUBSTITUATE PUMP: FLOW. At first, it is tested by means of the prefilter pressure sensor 33c, whether a test pressure TEST PRESSURE can be built up in the EB 1 within a defined time interval TIMEOUT.

If this is the case, the substituate pump 17 is stopped after this intermediate test has been passed. After that, an appropriate time PRESSURE BALANCE TIME is waited, so that a static pressure can build up. If the pressure has fallen below the minimum test pressure MIN TEST PRESSURE during the pressure balance period, the test is cancelled as an error has occurred.

Otherwise, the now following test step for the second roller of the pump rotor which differs from the first roller is performed. The pressure drop within a defined time period TESTTIME is determined. The absolute pressure change is considered, which must not exceed a maximum value MAXIMUM PRESSURE DROP.

In contrast to this, when testing the first roller, a time period TESTTIME is waited without evaluating the pressure drop.

After the test was passed, the arterial pressure rise is evaluated. If it exceeds the predetermined pressure drop MAXIMUM STANDSTILL LEAKAGE, no complete occlusion is present or achieved.

The following test step is only performed for the first roller of the pump rotor. In doing so, it is tested whether the non-return valve 23 in the substitute channel closes and seals.

In doing so, the previously built-up test pressure remains.

With the substitute pump 17, it is conveyed in reverse with the aim of conveying a maximum feed volume MAX FEED VOLUME, and at the same time the absolute pressure drop, measured at the pressure sensor 33c, is evaluated. It may not exceed a maximum value MAXIMUM PRESSURE CHANGE or its absolute value.

At the same time, the pressure in the blood cassette 2 may not rise (if this is the case, the substitute pump 17 rotates in the wrong direction).

As the compartment between the non-return valve 23 and the adjacent substitute pump 17 is very small (<3 ml), the volume which can be conveyed by the substitute pump 17 is usually limited. If the non-return valve 23 does not close, the conveyed volume depends on the maximum allowable pressure change MAXIMUM PRESSURE CHANGE. For a paticular type of an extracorporeal blood circuit 1 (in an air-free system), a pressure drop of 50 mbar approximately corresponds to a leakage of 250 µl.

In order to relieve or release the pressure in the EB 1, the arterial patient tube clamp 6, the venous patient tube clamp 7 and the valve V33 are energized.

The entire test is repeated for the other roller of the blood pump rotor. For this, at first the pressure relieve in the EB1 is waited (PRESSURE BALANCE TIME), subsequently, the rinse port is closed and it is continued with the step of positioning the blood pump rotor.

If an error occurs, the substitute pump 17 is stopped and the pressure in the EB 1 is relieved by opening the venous patient tube clamp 7 and by energizing the hydraulic valves V33, V28 and V19.

Tests by the applicant revealed that a leakage in the range of 5.5 ml/min to the exterior or into the SN chamber may be detected by means of this test. Furthermore, it may be possible to detect a non-pressing or a half-pressing state of the blood cassette 2.

If the test has been failed, in some embodiments according to the present invention a single repetition is envisioned. For safety reasons, it may be provided that a treatment of the patient is only possible once the test has been passed.

If the test has been failed, it may be necessary to remove or dismantle the tested blood cassette 2 and replace it by another blood cassette 2. The other blood cassette 2 is again filled and rinsed.

Examples of preset values of the above-named parameters are reproduced in the following parameter table (table 1):

TABLE 1

| Subtest | Parameters | Unit | Value |
|---|---|---|---|
| General parameters | PRESSURE BALANCE TIME | ms | 2000 |
| | SUBSTITUTE PUMP: FLOW | ml min$^{-1}$ | 500 |
| | PTESTSTART_EB | mbar | 67 |
| | PTESTSTART_HYD | mbar | 333 |
| Build up pressure | TEST PRESSURE | mbar | 1400 |
| | MIN TEST PRESSURE | mbar | 1250 |
| | TIMEOUT | ms | 15000 |
| Leak test | TESTTIME | ms | 5000 |
| | MAXIMUM PRESSURE DROP | mbar | 73 |
| | MAXIMUM STANDSTILL LEAKAGE | mbar | 400 |
| Test non-return valve 23 | MAX FEED VOLUME | ml | 5 |
| | MAXIMUM PRESSURE CHANGE | mbar | 20 |

Errors occurring while carrying out the present test and suggestions on how to fix them are reproduced in the following error table (table 2):

TABLE 2

| Subtest | Error |
|---|---|
| Build up pressure | TIMEOUT exceeded<br>→ SN valve 35 open<br>→ disposable not completely pressed |
| Leak test | MAXIMUM PRESSURE DROP exceeded<br>→ disposable leaky<br>MAXIMUM STANDSTILL LEAKAGE exceeded<br>→ roller incompletely engaged |
| Test non-return valve 23 | MAXIMUM PRESSURE CHANGE exceeded<br>→ non-return valve 23 leaky or<br>→ substituate pump 17 turns forward |

By the test of this embodiment, a blood cassette 2 which is leaky, e.g., due to insufficient pressing, may be identified.

Furthermore, a leakage sensor may be provided for detecting further or other leakages.

The second embodiment according to the present invention relates to a test for testing the tightness or sealing effect of the substituate connection. In this test, it is tested whether the substituate connection (automatic substituate connector 18b (ASC) with substituate port 18a) is tight (i.e., sealed) to the exterior. In addition, the seal of the disposable is tested for passage or patency.

For this, the blood cassette 2 is inserted into the treatment apparatus and pressed. The rollers of the substituate rotor are lowered or moved out. The hydraulics is available. The automatic substituate connector 18b connects. By means of the hydraulics, a pressure maintenance test is performed in a connected state of the blood cassette 2.

By means of this test, it is possible to detect a leakage occurring in the area of the automatic substituate connector 18b into the exterior in a range of 1 ml/min (corresponds to about 500 ml/treatment). Additionally, it is possible to determine an occlusion of an on-line access in the blood cassette 2.

In some embodiments according to the present invention a treatment of the patient is not possible unless the test has been passed. The test may be repeated as often as desired. Alternatively, the blood cassette 2 is removed and replaced by another blood cassette.

With the pressure-controlled fill program of the balancing chamber, pressure is built up in the area of the pressure sensor 37 against the substitute pump 17, which is not rotating, while the substituate connector is coupled and the valve V31 is open. This pressure may drop during a maintenance phase only within certain limits. In order to keep the liquid escape low in the event of a very leaky connection, in certain embodiments according to the present invention, a pre-test with low pressure is done first.

Furthermore, the patency between the hydraulics of the treatment apparatus 4 and the substitute pump 17 is tested by expecting a pressure drop at the pressure sensor 37 by rotating the substitute pump 17.

At or before the beginning of the test, the valve V31 and the valve V24 are closed.

The addition point 13 is closed, and so is the addition point 14. The substitute pump 17 is not running.

For beginning the test, a pressure-controlled fill program is started. In doing so, a pressure value LOW PRESSURE LIMITS is requested or demanded. A time period TIMEOUT of, e.g., 2 s is waited, during which, in the course of a rapid test, a minimum pressure LOW PRESSURE LIMITS should have built up or been kept. Should this not be the case, not even within the idle time TIMEOUT, a problem of the hydraulics is to be assumed.

The pressure measured by means of the pressure sensor 37 can be recorded.

Subsequently, the valve V31 is closed for a short period several times, e.g., three times (NV31), and opened again after lapse of an idle time TV31. In the meantime, a predetermined minimum pressure MINPRESSURE has to be kept. Subsequently, V31 remains open in order to tell whether a predetermined pressure drop is kept. If the predetermined pressure drop MAXPRESSUREDROP is exceeded, or if a predetermined minimum pressure MINPRESSURE is not kept, an error is to be assumed; the test is not passed then, possibly because the connection to the substituate port 18a is leaky. In this test section, the minimum hydraulic pressure may be monitored in order to exclude a pressure build-up by means of the fill program.

After this rapid (or quick) test, a pressure-controlled fill program with a pressure HIGH PRESSURE LIMITS is started for a patency test for pressure build-up. If or when a predetermined pressure TEST PRESSURE_HIGH is measured at the pressure sensor 37, it is advanced. If the minimum pressure at the sensor 37 is not built up within an idle time TEST PRESSURE-TIMEOUT, even though the hydraulics is available, again an error is to be assumed, for example, a very leaky substituate port 18a.

If the expected minimum pressure is, however, built up, a pressure-controlled fill program with low pressure limits LOW PRESSURE LIMITS is requested. In doing so, after waiting for an idle time PRESSURE BALANCE TIME, it has to be checked whether the pressure measured by means of the pressure sensor 37 falls below the expected minimum pressure MINTESTPRESSURE. If this is the case, an error has to be assumed which possibly stems from a leaky connection to the substituate port 18a.

When a dead time PRESSURE BALANCE TIME has expired, it is continued.

The pressure measured by means of the pressure sensor 37 may be recorded.

For moistening the substituate pump and for testing the blood cassette 2 for its patency, in a next step, the valve for the addition point 14 is opened. The valve for the addition point 13 remains closed. The substituate pump 17 is moved or rotated forward by a predefined volume SPVOLUME. For this, a low flow SUBSTITUATE PUMP: FLOW may be set.

If the pressure drop which is then determined by means of the pressure sensor 37 stays below an expected pressure drop or below a minimum pressure drop MINPRESSUREDROP, an error is assumed; possibly, the connection to the substituate port 18a is not patent.

Otherwise, the method advances to a leak test. For this, the valve of the addition point 14 is closed.

A pressure-controlled fill program with a pressure HIGH PRESSURE LIMITS may be prompted which again serves the monitoring of the connection to the substituate port 18a. After the idle time TIMEOUT has expired, during which a predetermined pressure TEST PRESSURE_HIGH has to be built up, otherwise a leaky connection to the substituate port 18a is assumed, it is advanced to a pressure build-up by means of a pressure-controlled fill program with low pressure limits as described above. If after a maintenance period MEASUREMENT INTERVAL has expired certain criteria such as pressure drop per second below a predetermined limit MAXLEAKAGE are met, the test is assumed as passed. Otherwise, or if an idle time MAXMAINTENANCEPERIOD is exceeded, an error is assumed; possibly, the connection to the substituate port 18a is leaky.

To determine the pressure value during the pressure maintenance phase, the following procedure may be used:

The pressure value is smoothed. In doing so, low-pass filtering with the smoothing factor SF=0.93 is utilized:

$$\text{VALUE\_new} = \text{VALUE\_old} * \text{SF} + \text{MEASURED VALUE} * (1-\text{SF})$$

This pressure value is updated in each slice; the test for lower deviation of the maximum leakage rate takes place every 2 seconds.

Examples of preset values of the above-named parameters are reproduced in the following parameter table (table 3):

TABLE 3

| Subtest | Parameters | Unit | Value |
|---|---|---|---|
| General parameters | PTESTSTART_HYD | mbar | 200 |
| | PRESSURE BALANCE TIME | ms | 2000 |
| | LOW PRESSURE LIMIT | mbar | 250 |
| | TEST PRESSURE_HIGH | mbar | 1100 |
| Rapid or quick test | TSWITCHTIME | ms | 300 |
| | TRAPIDTEST | ms | 1750 |
| | MAXPRESSUREDROP | % | 75 |
| | MINPRESSURE | mbar | 67 |
| | TV31 | ms | 250 |
| | NV31 | count | 3 |
| Patency test | MINTESTPRESSURE | mbar | 1050 |
| | TIMEOUT | ms | 2000 |
| | SUBSTITUATE PUMP: FLOW | ml min$^{-1}$ | 250 |
| | SPVOLUME | ml | 12 |
| | MINPRESSUREDROP | mbar | 133 |
| Leak test | TEST PRESSURE-TIMEOUT | ms | 2000 |
| | MAXLEAKAGERATE | mbar/s$^{-1}$ | 2.67 |
| | MEASUREMENT INTERVAL | s | 2 |
| | MAXMAINTENANCETIME | s | 25 |

Errors occurring in the present test and suggestions on how to fix them are reproduced in the following error table (table 4):

TABLE 4

| Subtest | Error |
|---|---|
| Rapid test | TIMEOUT exceeded<br>→ test pressure could not be built up<br>→ hydraulics problem<br>MAXPRESSUREDROP exceeded or fallen below MINPRESSURE<br>→ pressure drop too large: connection to the ASC very leaky |
| Patency test | TIMEOUT exceeded<br>→ connection to the ASC very leaky<br>→ or hydraulic problem<br>fallen below MINTESTPRESSURE<br>→ connection to the ASC very leaky<br>MINPRESSUREDROP not reached<br>→ connection to the ASC not patent |
| Leak test | TIMEOUT exceeded<br>→ connection to the ASC very leaky<br>→ or hydraulic problem<br>no falling below the MAXLEAKAGE during MAINTENANCE TIME<br>→ connection ASC-disposable leaky |

The third embodiment relates to a leak and function test of the addition points 13 and 14 for substitute in predilution respectively postdilution which are embodied as phantom valves. It is tested whether the phantom valves open, close and seal, or whether pressure gradients can be built up and maintained when opening or closing the phantom valves. Phantom valves that may have got stuck or close incorrectly can hereby be detected. This test can be repeated as often as desired. If it is not passed at all, the disposable may be removed and a new disposable may be inserted. Alternatively, service personnel may be informed. In certain embodiments according to the present invention, a treatment of the patient is not possible without the test being passed. This test may be performed also if the valves or addition points are not designed as phantom valves, but are of a different valve typ.

For performing this test, the blood cassette 2 is inserted and pressed as described above. The blood filter 19 is connected and filled on the disposable side and on the hydraulics side. The extracorporeal blood circuit 1 is filled and mainly free of air. The extracorporeal blood circuit 1 has preferably already passed the leak test of the first embodiment.

The arterial patient tube 8 and the venous patient tube 9 are each connected with the rinse port via a T-piece.

At the beginning of the test, the hydraulics is set into the Extended Bypass. At the same time, the valves V31 and V33 are energized and the pressure-controlled fill program is started. The valve V32 is closed.

The valve of the addition point 13 (predilution) is opened, the valve of the addition point 14 (postdilution) as well as the single-needle valve 35 remain closed. The arterial patient tube clamp 6 and the venous patient tube clamp 7 are or remain also closed.

If the pressure in the hydraulics exceeds a predetermined pressure PTESTSTART_HYD (measured by means of the pressure sensor 37), it is relieved or released with the assistance of the substituate pump 17 and a flow SUBSTITUATE PUMP: FLOW. The arterial patient tube clamp 6 and the venous patient tube clamp 7 may be opened herefor. In any case, the valve V33 is opened and substituate is conveyed until the hydraulic pressure (measured by means of the pressure sensor 37) has fallen below the pressure PTESTSTART_HYD. Subsequently, the substituate pump 17 is stopped and the valve V33 is closed again.

If the pressure in the hydraulic does not exceed the predetermined pressure PTESTSTART_HYD (measured by means of the pressure sensor 37), it is tested by means of the pressure sensor 33b whether the pressure measured in the extracorporeal blood circuit 1 exceeds the pressure PTESTSTART_EB (measured at the venous pressure sensor 33b). If this is the case, it is relieved by opening the valve V33 of the hydraulics; subsequently, the valve V33 is closed.

For testing, the target pressure TEST PRESSURE, measured by means of the pressure sensor 33b is now built up in the extracorporeal blood circuit 1 by means of the substituate pump 17 (SUBSTITUATE PUMP: FLOW). The target pressure should be achieved within the idle time PRESSURE BUILD-UP-TIMEOUT. If no such pressure build-up is detected by the pressure sensor 33b, it is assumed that the valve of the addition point 13 does not open or that the single-needle valve 35 stands open.

If no error occurs, the addition point 13 is closed, whereby the substituate pump 17 keeps running or rotating. Normally, the pressure in the extracorporeal blood circuit 1 does not change after waiting or lapse of an idle time PRESSURE BALANCE TIME during the subsequent idle time MEASUREMENT TIME. If, however, it rises by a value which is larger than the pressure rise MAXIMUM PRESSURE RISE (measured by means of the pressure sensor 33b), a problem with the valve(s) of the addition point(s) 13 and/or 14 may be assumed.

If the intermediate test is passed, the substituate pump 17 is stopped and the pressure in the extracorporeal blood circuit 1 is relieved by opening the venous patient clamp 7 and the addition point 13 and the idle time PRESSURE BALANCE TIME is waited.

The checking of the addition point 14 (postdilution) takes place analogously to the checking of the addition point 13 (predilution).

By opening the venous patient tube clamp 7 and by stopping the substituate pump 17, the pressure in the extracorporeal blood circuit 1 is relieved for the last time.

If an error occurs, the pressure in the extracorporeal blood circuit 1 is relieved by opening the venous patient tube clamp 7 and by stopping the substituate pump 17. Hemofiltration (HF) and hemodiafiltration (HDF) are no longer possible then.

Examples of preset values of the above-named parameters are reproduced in the following parameter table (table 5):

TABLE 5

| Subtest | Parameters | Unit | Value |
| --- | --- | --- | --- |
| General Parameters | PRESSURE BALANCE TIME | ms | 2000 |
| | SUBSTITUATE PUMP: FLOW | ml min$^{-1}$ | 100 |
| | PTESTSTART_EB | mbar | 67 |
| | PTESTSTART_HYD | mbar | 333 |
| Does valve 13 open? | TEST PRESSURE | mbar | 300 |
| | PRESSURE_BUILD-UP-TIMEOUT | ms | 10000 |
| Does valve 13 close? | MAXIMUM PRESSURE RISE | mbar | 4 |
| Do valve 13 & valve 14 seal? | MEASUREMENT TIME | ms | 5000 |
| Does valve 14 open? | PRESSURE BUILD-UP-TIMEOUT | ms | 5000 |
| | TEST PRESSURE | mbar | 300 |

Errors occurring in the present test and suggestions on how to fix them are reproduced in the following error table (table 6):

TABLE 6

| Subtest | Error |
| --- | --- |
| Does valve 13 open? | PRESSURE BUILD-UP-TIMEOUT exceeded<br>→ valve 13 not open |
| Does valve 13 close? | Pressure risen by MAXIMUM |
| Do valve 13 & valve 14 seal? | PRESSURE RISE<br>→ valve 13 open<br>→ valve 14 open<br>→ valve 13 and/or valve 14 leaky |
| Does valve 14 open? | TEST PRESSURE not reached<br>→ valve 14 not open |

The fourth embodiment relates to a leak test for the single-needle (SN) system. It is tested by means of test air whether the SN area is tight to the exterior.

For this test, the blood cassette 2 is inserted and pressed as described above. The single-needle valve 35 is closed. It is tested whether, with the blood cassette 2 being pressed, a pressure can be built up and maintained in the single-needle overpressure compartment and underpressure compartment. Leaks of the SN system of 500 ml/4 h and over can be detected.

If the test is failed, it may be repeated as often as desired. Alternatively, the SN operation may be stopped or inhibited. As always, the test may be repeated with a new disposable or service or maintenance personnel may be informed, if the test is failed.

In certain embodiments according to the present invention, it is possible to combine this test with the function test SN pneumatic system of the sixth embodiment.

The volume of liquid in the single-needle chamber is 10 ml at most.

At the beginning of the test, the bypass valve 352 is deenergized (=open) and the vent valve 354 is energized (=open). The single-needle valve 35 is being closed. The single-needle system is thus brought to ambient pressure, and so is the SN container. This is the case when the SN pressure sensors 358 and 356 deviate from zero by a value OFFSET_MAX at the most. This procedure has to be completed after an idle time TIMEOUT_INIT. Otherwise, the initial conditions could not be restored, for example, because the vent valve 354 and/or the bypass valve 352 do not open correctly.

For the leak test, the vent valve 354 and the bypass valve 352 are being closed for building up a test pressure. Subsequently, an idle time PRESSURE BALANCE TIME_SHORT is waited and after that the initial mass (entire air mass) in the single-needle system is calculated with the following formula (equation for ideal gases, isothermal):

$$m = \frac{pV}{R_S T} \quad m[\mu g] = \frac{p[Pa] \cdot V[mm^3]}{R_S \left[\frac{J}{kg \cdot K}\right] \cdot T[K]}$$

$$M_{ges} = m_{over} + m_{under} = \frac{p_{over} \cdot V_{over} + p_{under} \cdot V_{under}}{T \cdot R_S}$$

$R_s$=spec. gas constant for dry $$air = 287 \frac{J}{kg \cdot K}$$

$p_{over}$=pressure in the overpressure compartment (abs.)=measured with pressure sensor 358

$p_{under}$=pressure in the underpressure compartment (abs.)=measured with pressure sensor 356

$V_{over}$=volume of the overpressure compartment=87 ml $V_{under}$=volume of the underpressure compartment=308 ml T=ambient temperature (K)=measured with temperature sensor 362

The SN compressor 350 is started with a voltage SNCOMPRESSOR: VOLTAGE, which is tantamount with a compressor rate SNCOMPRESSOR: RATE. In the closed system, a pressure (measured by means of the pressure sensor 358) which is equal to or above a test pressure TEST PRESSURE, is built up hereby within an idle time TIMEOUT_DP. If or when this pressure was successfully built up, the SN compressor 350 is stopped and the idle time PRESSURE BALANCE TIME_LONG is waited. Subsequently, the air mass (M_ges(tStart)) in the SN system is calculated after the pressure build-up and compared with the take-off or start mass. The mass difference M_ges_0−M_ges (tStart) must thereby not fall below a value DM_BUILD_FALL and not exceed a value DM_BUILD_RISE. Otherwise, the mass change in the system during the pressure build-up is too great.

For leakage measurement, the air mass (M_ges_(tEnd)) in the system is calculated again after an idle time MEASUREMENT TIME and compared with the take-off mass from the beginning of the pressure maintenance test (M_ges(tStart)). The absolute value of the mass difference M_ges (tStart)−M_ges (tEnd) must thereby not exceed a value DM_TEST_MAX. If it exceeds this value, the mass change taking place in the system during the pressure maintenance test is too large.

An evaluation of the mass loss and no direct evaluation of the pressure change of the respective compartments may be based on an allowable (as it cannot be excluded) slight leakage of the SN compressor from the overpressure compartment to the underpressure compartment.

For completing the test, the bypass valve 352 is switched off or deenergized, and the single-needle system is aerated by energizing the vent valve 354.

Examples of preset values of the above-named parameters are reproduced in the following parameter table:

TABLE 7

| Subtest | Parameters | Unit | Value |
|---|---|---|---|
| General Parameters | PRESSURE BALANCE TIME_LONG | s | 5 |
|  | PRESSURE BALANCE TIME_SHORT | s | 1 |
| Restore initial conditions | OFFSET_MAX | mbar | 47 |
|  | TIMEOUT_INIT | s | 10 |
| Test pressure build-up for leak test | SNCOMPRESSOR: VOLTAGE | V | 4 |
|  | TEST PRESSURE | mbar | 950 |
|  | TIMEOUT_DP | s | 60 |
| Mass change after pressure build-up | DM_BUILD_FALL | mg | −15 |
|  | DM_BUILD_RISE | mg | 10 |
| Mass change in the pressure maintenance phase | MEASUREMENT TIME | s | 15 |
|  | DM_TEST_MAX | mg | 1.5 |

Errors occurring in the present test and suggestions on how to fix them are reproduced in the following error table (table 8):

TABLE 8

| Subtest | Error |
|---|---|
| Restore initial conditions | TIMEOUT_INIT reached<br>→ valve 354 does not open (correctly) or<br>→ bypass-valve 352 does not open (correctly) or<br>→ offset of the pressure sensors too great (sensors defect) |
| Test pressure build-up for leak test | TIMEOUT_DP reached<br>→ the test pressure could not be built up<br>→ valve 354 not closed/leaky or<br>→ bypass valve 352 not closed or<br>→ single-needle valve 35 not closed |
| Mass change after pressure build-up | DM_BUILD_FALL reached<br>→ the mass change in the system during the pressure build-up was too great<br>→ valve 354 leaky or<br>→ single-needle valve 35 not closed<br>DM_BUILD_RISE reached<br>→ the mass change in the system |

TABLE 8-continued

| Subtest | Error |
|---|---|
| | during the pressure build-up was too great<br>→ container very leaky or<br>→ level of the SN chamber too high |
| Mass change in the pressure maintenance phase | DM_TEST_MAX exceeded<br>→ mass change in the system during the pressure maintenance test too great<br>→ container leaky and/or<br>→ SN chamber leaky |

The fifth embodiment relates to a function test of the non-return valve 23 in the substitute channel. This test may be a part of the above-discussed leak test of the first embodiment, as is described for the first embodiment. It is tested, whether the non-return valve 23 in the substitute channel is operative. A pressure which was built up before in the EB 1 must not drop despite the substitute pump 17 running or rotating in reverse. By means of this test, the migration of blood into the substitute channel and the contamination of the automatic substitute connector 18b (an on-line connector) with blood is advantageously prevented.

If the test is failed, it can be repeated once. A treatment of the patient is only possible if the test is passed.

For details on this method which is executable also independently of other tests, it is referred to its description above.

The sixth embodiment relates to a function test of the single-needle (SN) pneumatic system.

In this test, it is tested whether the single-needle compressor is running, whether the pneumatic valves switch, the pressure sensors work and whether the pneumatic system is tight on the machine side.

For this, a pressure gradient is built up in the single-needle system with a disposable being inserted and pressed, and optionally after a successfully completed T1 test. It is tested whether the pressure gradient is maintained within a predetermined time period or at least does not drop more than allowed.

If this test is not passed, it is in certain embodiments according to the present invention provided to inhibit a single-needle operation.

If during the test of an arbitrary embodiment according to the present invention a blood alarm occurs, the current test step is stopped or cancelled. In some embodiments according to the present invention, it is provided that the cancelled test be automatically repeated after clearing the alarm.

If an error message of the test step exists or is due when the alarm occurs, it is in some embodiments according to the present invention automatically deleted when the test step is repeated.

In certain embodiments, if no substitute is available (conductivity alarm/temperature alarm), the test or partial test is also cancelled and subsequently triggered anew.

If the conductivity LF is beyond a range of tolerance, no substitute is provided or made available in some embodiments according to the present invention.

In certain embodiments according to the present invention if the level in the venous chamber drops during a test, the test is cancelled. An exception hereof may be the leak test for the substituate connection.

If one of the function tests is failed or not passed, a confirmable alarm is generated in the event that an arterial optical detector (OD) displays dark (=blood enters the extracorporeal blood circuit). If an OD (venous) which is arranged in the venous section displays dark, the disposable should be removed.

The tests and subtests of the above illustrated embodiments may be arbitrarily combined, provided and as far as the person skilled in the art does not recognize this to be technically impossible.

In order to ensure that the respective relevant function tests are performed before the beginning of each treatment and that errors are detected, an accordingly programmed or configured function test monitor is used. It monitors the performance of the function tests and checks their results.

In some embodiments according to the present invention the method according to the present invention encompasses apart from the actual function tests—e.g., as described above—also the determination of the system offset of the fistula pressure sensors.

In some embodiments according to the present invention, if in the transition of the arterial optical detector (OD) to dark (=blood enters the extracorporeal blood circuit) it is detected that a function test was not or not successfully performed or passed, a corresponding blood alarm is generated. The alarm may possibly be resettable in order to bypass or neglect any temporary failures of the arterial OD by air bubbles or the like. This is, however, not always provided for or possible. The bypass time may be, for example, 0.25 s. If the arterial OD stays dark, in some embodiments according to the present invention no treatment is possible.

In addition, if a function test was not passed and the venous OD detects blood, a non-confirmable blood alarm is generated which compels dismantling the system.

In particular the approach for monitoring the SN system function test may deviate from this. If this test is recognized as failed (or not performed) during the transition of the venous OD to dark, a SN treatment is inhibited by setting a corresponding variable (e.g., E2_SN_Enable to SECURE_FALSE). During the transition of the arterial OD to dark, in some embodiments according to the present invention no control takes place.

If test errors occur, status variables and error variables may be set. Independent hereof, entries in error charts or error protocols may be generated. In both cases, both the performed test and the error condition may be saved, in particular in a readable way.

In some embodiments according to the present invention, if the function tests are not completed when the nominal flush volume is reached, the nominal flush or rinse volume is automatically raised by 50 ml. A corresponding message may be output.

Corresponding messages can be output when or if function tests are passed and/or failed.

REFERENCE NUMERAL LIST FOR FIGS. 1 AND 2

1 extracorporeal blood circuit
2 blood cassette
3 first fluid conduct of the automatic substituate connector 18b
4 treatment apparatus
5 second fluid conduct of the automatic substituate connector 18b
6 arterial patient tube clamp
7 venous patient tube clamp
8 arterial patient tube or arterial blood line 9 venous patient tube or venous blood line
10 third fluid conduct of the automatic substitute connector 18b
11 blood pump
11' brake device of the blood pump
13 addition point for substitute liquid (predilution)
14 addition point for substitute liquid (postdilution)
15 arterial air-blood detector
17 substitute pump
17' brake device of the substitute pump
18a automatic substitute port
18b automatic substitute connector
19 blood filter
19a blood chamber
19b dialysate chamber
21 venous air separation chamber
23 non-return valve of the substitute channel
25 venous air-blood detector
26 source of compressed air
27 blood inlet of the blood filter 19
28 control and/or regulating device
29 blood outlet of the blood filter 19
31a dialyzing liquid supply line
31b dialysate drain line
33a,b pressure sensors
33c prefilter pressure sensor
35 single-needle valve
37 pressure sensor
40 hydraulic balance chamber
41 dialyzing liquid inlet of the blood filter 19
43 dialysate outlet of the blood filter 19
45 drain line
47 sterile air supply
V19 valve of the dialysate drain line 31b
V24 valve of the dialyzing liquid supply line 31a
V25 valve of the dialysate drain line 31b
V28 valve of the drain line 45
V31 valve of the first fluid conduct 3 of the automatic substitute connector 18b
V32 valve of the second fluid conduct 5 of the automatic substitute connector 18b
V33 first valve of the drain line 45
V42 valve of the sterile air supply 47
V43 valve of the third fluid conduct 10 of the automatic substitute connector 18b
H33 rinse port
P03 ultrafiltration pump
100 air diffuser panel
200 pneumatic unit
300 single-needle unit
301 ventilation inlets and outlets
350 single-needle compressor
352 bypass valve
354 vent valve
356 pressure sensor
358 pressure sensor of the SN line
360 absolute pressure sensor
362 temperature sensor in the SN pressure vessel
370 connector, connects the single-needle unit 300 with the single-needle chamber of the blood cassette 2

The invention claimed is:

1. A method for testing at least one function of (i) a medical functional device which is inserted in and connected and pressed with a medical treatment apparatus, or (ii) the treatment apparatus, wherein between a hydraulic device or a pneumatic unit of the medical treatment apparatus and the functional device at least one fluid connection is established, the method comprising:
   a) building up a pressure via the hydraulic device or the pneumatic unit within the at least one fluid connection;
   b) measuring the pressure prevailing within the at least one fluid connection or measuring a pressure change within the at least one fluid connection;
   c) determining the at least one function of the at least one of the medical functional device or the medical treatment apparatus based on a comparison of the prevailing pressure or the measured pressure change with previously saved values, threshold values, ranges or changes thereof;
   d) conveying a predetermined feed volume (MAX FEED VOLUME) within the at least one fluid connection using a substitute pump running in reverse against a non-return valve which is provided within a substitute channel;
   e) determining the pressure change within the at least one fluid connection; and
   f) determining a non-return function of the non-return valve, if a determined pressure drop is not equal to or higher than a maximum pressure drop (MAX PRESSURE DROP) or not higher than a predetermined absolute value of a pressure change (MAXIMUM PRESSURE CHANGE).

2. The method according to claim 1, wherein the step a):
is executed based on measuring a default pressure value upon applying a pre-pressure within the at least one fluid connection, wherein the pre-pressure is lower than the pressure to be built up.

3. The method according to claim 1, further comprising:
filling a blood filter the functional device is connected with.

4. The method according to claim 1, further comprising:
building up the pressure via the substitute pump of the medical treatment apparatus.

5. The method according to claim 4, further comprising:
building up the pressure against the substitute pump when it is not running.

6. The method according to claim 1, further comprising:
determining a pressure drop or a pressure rise within the at least one fluid connection; and
determining a patency or a tightness of the at least one fluid connection or of the functional device based on a comparison of the determined pressure drop or pressure rise with previously saved values, threshold values, ranges or changes thereof.

7. The method according to claim 1, further comprising:
conveying a predetermined feed volume (MAX FEED VOLUME) within the at least one fluid connection with the substitute pump running in reverse against the non-return valve which is provided within the substituate channel;
determining a pressure change within the at least one fluid connection; and
determining that the substitute pump conveys or conveyed forwards, if a determined pressure rise is higher than a maximum pressure rise (MAX PRESSURE RISE) or higher than a predetermined absolute value of a pressure change (MAXIMUM PRESSURE CHANGE).

8. The method according to claim 1, further comprising:
detecting a current pressure value (VALUE_new) based on previous pressure value (VALUE_old), on a measured value (MEASURED VALUE) and on a predetermined smoothing factor (SF) according to the formula:

$$VALUE\_new = VALUE\_old * SF + MEASURED\ VALUE * (1-SF),$$

wherein:
VALUE_new is a current pressure value;
VALUE_old is the pressure value which is already present;
SF is a smoothing factor; and
MEASURED VALUE is a current measured value of the pressure.

9. The method according to claim 8, wherein the smoothing factor (SF) is in a range between 0.9 to 0.96.

10. The method according to claim 1, further comprising:
connecting the medical functional device to an extracorporeal blood circuit; and
filling the extracorporeal blood circuit before building up the pressure.

11. The method according to claim 1, wherein the at least one function tested is at least one of opening, closing, sealing and whether pressure gradients can be build up and maintained when opening or closing valves.

12. The method according to claim 1, wherein at least one function, in particular opening, closing or sealing, of at least one of the following components is tested:
a valve for an addition point for substituate in predilution;
a valve for an addition point for substituate in postdilution;
a single-needle valve;
a non-return valve in the substituate channel; and
an automatic substituate connector.

13. The method according to claim 1, wherein the method is executed before the beginning of a treatment of a patient during which the functional device is used.

14. The method according to claim 1, further comprising:
based on the results of the testing of the at least one function of the at least one of the medical functional device or the medical treatment apparatus, at least one of blocking treatment modalities and restricting treatment parameters.

15. The method according to claim 1, wherein the medical functional device is a blood cassette, and wherein the treatment apparatus is a blood treatment apparatus.

16. The method according to claim 1, further comprising:
outputting a signal about the at least one tested function based on the comparing of the prevailing pressure or the measured pressure change with the previously saved values, threshold values, ranges or changes thereof.

17. A detection device at least one of programmed and configured to execute or prompt the method according to claim 1.

18. The detection device according to claim 17, comprising at least one displaying device configured to display a result of the execution of the method.

19. The detection device according to claim 17, comprising at least one alarm device configured to output an alarm in the event that the result of the execution of the method is not in a predetermined range.

20. The detection device according to claim 17, which is programmed and/or configured to influence or prompt the treatment apparatus such that at least one treatment option or predetermined treatment parameter is not executable if a functionality of at least one of the functional device, the treatment apparatus or of a component of the medical functional device or the medical treatment apparatus is lacking.

21. The detection device according to claim 20, wherein the detection device effects the treatment apparatus or is programmed such that the at least one treatment option is not executable.

22. The detection device according to claim 17, wherein the detection device comprises a control apparatus or a function test monitor.

23. A medical treatment apparatus which comprises at least one detection device according to claim 17 or is in signal transmission or is connected for signal transmission with the at least one detection device.

24. The medical treatment apparatus according to claim 23, wherein the medical treatment apparatus is embodied as a blood treatment apparatus for apheresis, dialysis, hemodialysis, hemofiltration, or hemodiafiltration.

25. A digital storage medium in the form of a disk, CD, DVD, EPROM, or other machine readable medium with electronically readable control signals, configured for interacting with a programmable computer system such that the method according to claim 1 is prompted.

* * * * *